United States Patent [19]  [11]  4,329,297
Rossi et al.  [45]  May 11, 1982

[54] PROCESS FOR PREPARING SATURATED ω-AMINO ACIDS

[75] Inventors: Pietro P. Rossi, Garlasco; Mario De Gaetano, Cesano Maderno, both of Italy

[73] Assignee: SNIA VISCOSA Societa' Nazionale Industria Applicazioni Viscosa S.p.A., Milan, Italy

[21] Appl. No.: 131,106

[22] Filed: Mar. 18, 1980

[30] Foreign Application Priority Data

Mar. 21, 1979 [IT] Italy ............................... 21163 A/79

[51] Int. Cl.³ ............................................... C11C 1/00
[52] U.S. Cl. ..................................... 260/404; 562/553
[58] Field of Search .......................... 260/404; 562/553

[56] References Cited

U.S. PATENT DOCUMENTS 2,777,873  1/1957  Hasek .................................... 260/404
4,054,588  10/1977 Siclari et al. .......................... 260/404
4,085,127  4/1978  Siclari et al. .......................... 260/404

Primary Examiner—John F. Niebling
Attorney, Agent, or Firm—Hubbell, Cohen, Stiefel & Gross

[57] ABSTRACT

A process for continuous or batch preparation of an ω-amino-acid is described, comprising the imination of an unsaturated aldehyde acid, the catalytic reduction in a single hydrogenation step of the imine of the ethylenically unsaturated straight chain ω-aldehyde acid in the presence of ammonia and an alkaline metal hydroxide whereby the alkaline salt of the imine is obtained, and the acidification of the alkaline salt of the ω-amino acid. The imine of formyl alkenoic acid is prepared at most at room temperature adding the acid to an ammonia solution of above 10%, then adding NaOH solution to the ammonia solution. The reductive imination is effectuated in two steps, first at 100°–150° C. and the second at 150°–180° C. under a 20–70 Ate pressure in the presence of a nickel catalyst. High yield and only few by-products are obtained.

19 Claims, No Drawings ved with $H_2$ both at the imino function and at the
PROCESS FOR PREPARING SATURATED ω-AMINO ACIDS

BACKGROUND OF THE INVENTION

This invention relates to an improved process for preparing, in a single hydrogenation step, saturated omega-amino acids from olefinically unsaturated omega-aldehyde acids.

This invention also refers to the omega-amino acids thus obtained.

The industrial importance of these products is well known and does not require any evidence.

It will be enough to recall for example the wide use of these amino acids as monomers for the manufacturing of polyamides used as plastics in the textile field for the manufacture of polyamide fibers and yarns.

The omega-amino acids to which this invention refers are defined by the general formula (I) $H_2N-(CH_2-)_{n+1}COOH$ wherein "n" is an integer varying from 4 to 16 and preferably 4–10.

From U.S. Pat. No. 4,054,588 it is known the conversion, in a single hydrogenation step of an unsaturated, straight chain ω-aldehyde acid into the corresponding ω-amino acid. More particularly in the U.S. Pat. No. 4,054,588 the unsaturated omega aldehyde acid is converted to the corresponding imino acid and then is reduced with $H_2$ both at the imino function and at the ethylenic double bond in a single step in the presence of a hydrogenation catalyst comprising a transition metal of one of the first two subgroups of group VIII of the periodic system of the elements, that is one chosen from Ru, Os, Co, Rh, Ir. The best results are obtained by using ruthenium and rhodium supported on carbon, obtaining yields of about 80% or somewhat higher of the stoichiometric yield. It was also known from the Italian Pat. No. 998227 that carrying out the reduction of the imine function of the unsaturated aldehyde acid in water and alkali and using a nickel catalyst, under particular conditions the unsaturated amino acid is thus obtained, while changing the conditions, for example increasing temperature, resulted in addition to small amounts of the saturated amino acid, in the production of many by-products as well.

It has now been surprisingly found that this conversion, in a single hydrogenation step, of the unsaturated straight chain acid to the corresponding saturated amino acid, can be carried out with high yields ($\geq 90\%$) and with much less production of undesired by-products in particular operating conditions also in the presence of metallic nickel or a nickel compound, thereby obtaining not only improved yields with respect to Ru, Rh, etc. but also advantages of economical nature. A further advantage will result clearly considering that by carrying out the reaction in two hydrogenation steps as disclosed in the Italian Pat. No. 998227 it is necessary to isolate, regenerate and recycle two catalysts, with possible mixing thereof, in which case, not only may the product be lost, but the whole catalyst may have to be necessarily replaced as well.

SUMMARY OF THE INVENTION

An object of the present invention is a continuous or a batch process for preparing an omega-amino acid of formula (I) with high yields ($\geq 90\%$) whereby obtaining few by-products only, by iminating the unsaturated aldehyde acid and subsequently catalytically reducing it in a single step by hydrogenation of the imine of the ethylenically unsaturated, straight chain omega-aldehyde acid in the presence of ammonia and an alkaline metal hydroxide to convert the ammonium salt of the imine of the aldehyde acid to the corresponding alkaline salt, and subsequently acidifying by known methods the obtained alkaline salt of the omega-amino acid, characterized in that said reductive imination is carried out under a pressure of from 20 to 70 Ate and in the presence of a catalyst chosen from metallic nickel and a compound thereof, this reduction being carried out in two steps at two different temperature ranges and particularly, in the first step at a temperature of from 100° to 150° C. and in the second step at a temperature of from 150° to 180° C. In order to obtain high reaction efficiency, it is essential that in the second step at 150°–180° C. the total pressure of the system be such as to have a molar fraction of $NH_3$ in the liquid phase not much lesser than that present in the first step, at 100°–150° C.

DESCRIPTION OF THE PREFERRED EMBODIMENTS OF THE INVENTION

Preferably the ammonia is present in a concentration of from 15 to 50% by weight of the whole solution. Preferably the reductive imination according to the invention is carried out during a period of time of up to 10 hours.

As metallic nickel Raney-nickel is suitably employed and as the nickel compound, the compound obtained by decomposition of a salt thereof with a monocarboxylic acid, preferably formic acid, is used.

More particularly, the ethylenically unsaturated, straight chain aldehyde acid useful as starting compound according to the present invention for obtaining the saturated omega-amino acid of formula (I), can comprise from 1 to 3 olefinic double bonds and corresponds therefore to the following general formula (II)

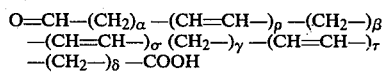

wherein
 α, β, γ, δ = integers, equal or different from one another, chosen from 1, 2 and 4;
 ρ, σ, τ = integers, equal or different from one another, chosen from 0 and 1; provided that the sum $\rho + \sigma + \tau = 1$, 2 or 3;
 the sum $\alpha + \beta + \gamma + \delta + \rho + \sigma + \tau = \eta$, η being an integer comprised between 3 and 11.

Non limitative examples of such acids are:
7-formyl-4-heptenoic acid, wherein
 $\alpha = 2, \beta = 2, \gamma = 0, \delta = 0, \rho = 1, \sigma = 0, \tau = 0, \eta = 5$,
11-formyl-4,8-undecadienoic acid, wherein
 $\alpha = 2, \beta = 2, \gamma = 2, \delta = 0, \rho = 1, \sigma = 1, \tau = 0, \eta = 8$, etc.

Actually the saturated imino acid is obtained, according to the invention, in the alkaline salt form thereof by treatment with ammonia and an alkaline metal hydroxide in aqueous solution, according to a reaction sequence carried out under atmospheric pressure, which reaction sequence comprises a first step carried out at a temperature comprised between the room temperature and one lower than the room temperature, wherein the aldehyde acid is added to an aqueous solution of ammonium hydroxide (but not conversely), and then this solution is treated with soda (and not conversely) and the aqueous solution thus obtained is hydrogenated in the presence of a nickel catalyst at a temperature and pressure as stated herein above. Said reactions (see U.S.

Pat. No. 4,054,588) can also be carried out for example under particular conditions in a single step, introducing the aldehyde acid by means of a high pressure metering pump and an inlet pipe, the cross section of which is such as to allow for an outlet flow rate of the aldehyde acid under the autoclave port for $H_2O$—$NH_3$ of above 100 cm/minute and introducing simultaneously the aqueous solution of sodium hydroxide into the autoclave already containing the nickel catalyst by means of a second metering pump, or it is possible first to form the whole or part of the alkaline salt of the imino acid, and then carry out the hydrogenation in a single hydrogenation step, whereby in any case the alkaline salt of the desired saturated amino acid is obtained, from which subsequently the acid is obtained by treatment with an acid compound, according to known methods.

When operating according to the characterizing parameters of the invention, that is if the sodium salt of the imine of the unsaturated aldehyde acid is being prepared out of the tank in which the hydrogenation is carried out, it is necessary, for obtaining high yields, to respect the following sequence of operations: it is the aldehyde acid which must be introduced into the ammonia and not viceversa, and the alkaline hydroxide has to be added to the imino solution and not viceversa.

In the case in which the aldehyde acid is introduced into the autoclave in which the hydrogenation is carried out, it is necessary to have a such system as to allow the aldehyde acid to leave the pipe conducting it to the autoclave, under the level of the liquids contained therein and at a flow rate not lower than 100 cm/minute.

In both cases the temperature profile, and thus the operating pressure, should ensure a molar concentration of ammonia in the liquid phase not lower then 10% by weight.

The nickel catalysts, which ensure high yields in this process for preparing omega-amino alkanoic acids, are preferably of two types: the first one is nickel obtained by thermal decomposition of nickel formate at 220°–240° C. in cyclododecane, the second one is Raney nickel suitably heat-treated before its use with an acqueous solution of formic acid at a concentration varying between 2 and 80% by weight.

The temperature of this treatment varies according to the type of Raney nickel employed and is comprised between 40° and 100° C.

A further object of the present invention are the omega-amino acids of formula (I) obtained by the above disclosed process.

The following examples are illustrative but not limitative, all the percentages are intended as being by weight.

EXAMPLE I 15 g of nickel catalyst as from formate (obtained by thermal decomposition of nickel formate suspended in cyclododecane and heated at 230°–235° C.), in 50% aqueous suspension, 266 g of an aqueous ammonia solution of 28% by weight under hydrogen pressure up to 20 Ate, are added at room temperature to a 3 liters AISI 316 steel autoclave equipped with high rate stirrer, temperature control system and volumetric metering pump.

Heating is started under stirring, and is maintained until the internal temperature reaches 135° C. and the pressure reaches 40 Ate, then 800 g of an aqueous ammonia solution comprising 530 g of 36% aqueous ammonia, 160 g of raw 11-formyl-4,8-undecandienoic acid (of 64%) and 110 g of 30% sodium hydroxide are fed at 50 ml/min.

During the feeding, the heating of the autoclave is controlled so as to maintain a temperature of 130°–140° C. and a pressure of 45 Ate.

Upon completion of the feeding, the temperature is slowly brought to 180° C. and the pressure to 50 Ate and these values are maintained for 6 hours.

After this period of 6 hours, the solution present at the bottom of the autoclave is discharged, nickel is separated, and the solution is left to evaporate for removing excess ammonia. The solution of the sodium salt of the amino acid is extracted with toluene for partly removing the by-product. From the aqueous solution containing the sodium salt of the amino acid, 97 g of 12-amino-dodecanoic acid are obtained corresponding to a yield of about 94% of the stoichiometric of the 11-formyl-4,8-undecadienoic acid contained in the starting mixture, by treatment with aqueous sulphuric acid at atmospheric pressure and at a temperature of 70° C. so as to obtain a pH value comprised between 10 and 11 (these pH values correspond to a temperature of 20° C.).

EXAMPLE II

To the autoclave disclosed in example 1, there are charged at room temperature, 15 g of nickel catalyst from formate (obtained as in example I) but regenerated after a use cycle by washing with ethyl alcohol at 70° C. and with water. Under the same temperature and pressure conditions of example I a solution is fed at 50 ml/min having the following composition:

530 g of a 36% aqueous $NH_3$ solution, 150 g of pure 11-formyl-4,8-undecadienoic acid (99.5%) (obtained by molecular distillation of the raw product), and 97.2 g of 30% aqueous solution of NaOH. After completion of the feeding, the temperature is increased from 140° to 175° C. during a period of 60 minutes and the pressure is increased from 40 to 60 Ate. After 120 minutes under the above mentioned reaction conditions, the hydrogen up-take is interrupted; the solution is cooled, the catalyst is filtered off and the solution is evaporated for removing the ammonia still present. By acidifying with sulphuric acid at a controlled pH of from 10 to 11 (set forth at 20° C.), the omega-amino-dodecanoic acid precipitates out of the aqueous solution, which precipitate, after filtration washing with water and drying, weights 146.7 g and has a 98% purity. The molar yield is of 94%.

EXAMPLE III

A 1500 ml AISI 316 autoclave equipped with a stirrer and a suction pipe immersed to a level corresponding to a volume of 1000 ml, is connected to a pressurized vessel containing a 20% by weight nickel suspension (obtained from Raney nickel by treatment at 100° C. with an aqueous solution of formic acid of from 5 to 20% by weight of the nickel) which vessel opens up intermittently by means of a valve actuated by a timer device, thus feeding the nickel suspension to the autoclave. This first autoclave is connected through a feeding pipe to a second autoclave of 1500 ml provided with stirring and maintained at the same pressure as the first autoclave.

After having charged the autoclaves at room temperature as hereinbefore described with 30 g of nickel in a 50% aqueous suspension and 220 g of 36% solution of $NH_3$, the temperature is brought to 130° C. and the pressure to 60 Ate; than to the first autoclave a solution comprising:

19% of sodium salt of 11-imino-4,8-undecadienoic acid, 5.3% of sodium salt of by-products of 11-imino-4,8-undecadienoic acid, 0.18% of NaOH, 23.9% of NH₄OH, 51.62% of H₂O and 100 g/hour of nickel suspension, is fed at a flow rate of 600 ml/hour by means of piston metering pump.

In this manner after 1 hour and a half the first autoclave is filled up and the solution starts to pass into the second autoclave where, after an additional hour and a half, the discharge of the hydrogenated solution begins, the solution passes then through a filter wherein the catalyst is removed. During the reaction, in the second autoclave, a temperature of 160°–180° C. and a total pressure of 60 Ate are maintained, by continuously feeding hydrogen from a gas cylinder.

The content of residual olefinical double bonds and of omega-amino-dodecanoic acid in the hydrogenated solution with respect to the starting composition is determined at time intervals initiating from the moment in which the solution starts to leave the second autoclave whereby the following results are obtained.

| TIME | RESIDUAL DOUBLE BONDS | OMEGA-AMINO-DODECANOIC ACID | MOLAR YIELD |
|------|----------------------|------------------------------|-------------|
| 1h   | <1%                  | 16,05%                       | 90,7%       |
| 4h   | "                    | 16,2%                        | 91,6%       |
| 12h  | "                    | 16,5%                        | 93,3%       |
| 24h  | "                    | 16,1%                        | 91,06%      |
| 36h  | "                    | 16,0%                        | 90,5%       |

EXAMPLE IV

Example I was repeated except that Raney nickel was used as catalyst under the same operative conditions of temperature and time intervals, and that the pressure was increased in the second step to 70 Ate.

The yield of the corresponding omega-amino acid was of 92% of the stoichiometric.

We claim:

1. A process for preparing, continuously or in batches an omega-amino acid of the general formula (I) $H_2N-(CH_2-)_{n+1}COOH$, wherein "n" is an integer from 4 to 16, in a high yield of 90% or more with very few by-products, comprising:
   (1) iminating an unsaturated omega-aldehyde acid to produce an imine of said omega-aldehyde acid, said imine of said omega-aldehyde acid being prepared by adding said omega-aldehyde acid to an ammonia solution wherein the ammonia concentration exceeds 10% and, thereafter adding an alkaline hydroxide solution to said ammonia solution, said imination being carried out at room temperature or below;
   (2) catalytically reducing in a single hydrogenation step said imine of said omega-aldehyde acid in the presence of ammonia and an alkaline metal hydroxide thereby forming a alkaline salt of said imine of the omega-aldehyde acid, which is subsequently reduced to the corresponding alkaline salt of the omega-amino acid, wherein said reductive imination is carried out under pressure of from 20 to 70 Ate in the presence of a nickel catalyst and, wherein said reduction is carried out in two steps at two different temperature ranges, the first step at a temperature of from 100° to 150° C. and the second step at a temperature of from 150° to 180° C.
   (3) acidifying the thus obtained alkaline salt of the omega-amino acid thereby producing said omega-amino acid.

2. A process according to claim 1, wherein said alkaline solution is sodium hydroxide solution.

3. A process according to claim 1, wherein the second step of the reduction is carried out so that the total pressure of the system is such that the molar fraction of NH₃ in the liquid phase is not much below the molar fraction of NH₃ in the liquid phase in the first step of the reduction.

4. A process according to either claim 1 or 2, wherein said hydrogenation is carried out for a period of up to 10 hours.

5. A process according to claim 1, wherein said nickel catalyst is either Raney nickel treated with formic acid or nickel obtained by controlled thermal decomposition of a salt thereof with a monocarboxylic acid.

6. A process according to claim 5, wherein said monocarboxylic acid is formic acid.

7. A process acording to claim 1, wherein the preparation of the alkaline salt of the imino acid of said omega-aldehyde acid and the hydrogenation thereof are carried out in a single reaction step.

8. A process according to claim 7, wherein the hydrogenation is carried out in an autoclave.

9. A process according to claim 8, wherein said omega-aldehyde acid is fed to the hydrogenation autoclave at a rate of 100 cm/min or more.

10. A process according to claim 1, wherein the preparation of the alkaline salt of said imine of said omega-aldehyde acid is carried out in a reaction step and, thereafter, the hydrogenation of said alkaline salt of said imine of said omega-aldehyde acid is carried out in a subsequent reaction step.

11. A process according to claim 1, wherein the yield of said omega-amino acid, with respect to the starting unsaturated omega-aldehyde acid, is at least 90% of the theoretical value.

12. A process according to claim 1, wherein "n" is an integer of from 4 to 10.

13. A process according to claim 12, wherein said omega-aldehyde acid is selected from the group consisting of 7-formyl-4-heptenoic acid and 11-formyl-4,8-undecadienoic acid.

14. A process for preparing a saturated omega-amino acid of the general formula $H_2N-(CH_2-)_{n+1}COOH$, wherein "n" is an integer in a high yield of 90% or more with very few by-products, comprising:
   (1) iminating an unsaturated omega-aldehyde acid of the general formula:

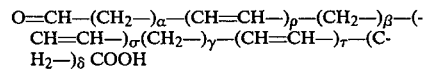

wherein
   $\alpha,\beta,\gamma,\delta$ = integers, equal or different from one another, chosen from 1, 2 and 4;
   $\rho,\sigma,\tau$ = integers, equal or different from one another, chosen from 0 and 1; provided that the sum $\rho+\sigma+\tau=1$, 2, or 3; and the sum $\alpha+\beta+\gamma+\delta+\rho+\sigma+\tau=\eta$,
   $\eta$ = an integer comprised between 3 and 11,
   said imine of said omega-aldehyde acid being prepared by adding said omega-aldehyde acid to an ammonia solution wherein the ammonia concentration exceeds 10% and, thereafter adding an alkaline hydroxide solution to said ammonia solution, said imination being carried out at room temperature or below;

(2) catalytically reducing in a single hydrogenation step said imine of said omega-aldehyde acid in the presence of ammonia and an alkaline metal hydroxide thereby forming a alkaline salt of said imine of the omega-aldehyde acid, which is subsequently reduced to the corresponding alkaline salt of the omega-amino acid, wherein said reductive imination is carried out under pressure of from 20 to 70 Ate in the presence of a nickel catalyst and, wherein said reduction is carried out in two steps at two different temperature ranges, the first step at a temperature of from 100° to 150° C. and the second step at a temperature of from 150° to 180° C.; and (3) acidifying the thus obtained alkaline salt of the omega-amino acid thereby producing said omega-amino acid.

15. A process according to claim 14, wherein said alkaline hydroxide solution is sodium hydroxide solution.

16. A process according to claim 14, wherein the imination and hydrogenation reactions are carried out in a single reaction step.

17. A process according to claim 14, wherein preparation of the alkaline salt of said imine of said omega-aldehyde acid is carried out in a reaction step and, thereafter, the hydrogenation of said alkaline salt of said imine of said omega-aldehyde acid is carried out in subsequent reaction step.

18. A process according to either claim 1 or claim 14, wherein the hydrogenation catalyst is supported on a support selected from the group consisting of carbon, calcium carbonate, alumina, silica, and silica alumina.

19. A process according to claim 14, wherein the hydrogenation is carried out for a period of up to 10 hours.

* * * * *